United States Patent [19]
Riggs et al.

[11] 3,991,375
[45] Nov. 9, 1976

[54] ANALOG SCANNER

[76] Inventors: E. Russell Riggs, 8637 N. 56th St., Paradise Valley, Ariz. 85253; Joseph Kolar, 4039 N. 57th Place, Phoenix, Ariz. 85018

[22] Filed: Oct. 17, 1975

[21] Appl. No.: 623,483

[52] U.S. Cl. ............................. 328/75; 328/4; 328/130; 324/61 R; 239/64; 73/73; 317/DIG. 3
[51] Int. Cl.² .................. H03K 17/56; B05B 12/08
[58] Field of Search ................ 328/75, 130, 4; 324/61 R, 61 P; 73/73; 239/63, 64; 317/DIG. 3

[56] References Cited
UNITED STATES PATENTS

| | | |
|---|---|---|
| 2,812,976 | 11/1957 | Hasenkamp ............... 317/DIG. 3 |
| 3,037,704 | 6/1962 | Kinigsberg et al. ............ 239/63 |
| 3,504,189 | 3/1970 | McHenry ...................... 328/75 |
| 3,599,867 | 8/1971 | Griswold et al. .............. 239/63 |
| 3,777,976 | 12/1973 | Milovancevic ............... 73/73 X |
| 3,824,480 | 7/1974 | Eshraghian ................ 328/130 X |
| 3,876,950 | 4/1975 | O'Connor ................... 328/130 |

*Primary Examiner*—John S. Heyman
*Attorney, Agent, or Firm*—Warren F. B. Lindsley

[57] ABSTRACT

An analog scanner for the control of various industrial, agricultural and domestic operations and processes comprising at least two pairs of probes utilized for measuring a physical property of a medium therebetween including at least a pair of control signal sources, at least a pair of reference level controllers, at least a pair of sensor selectors, and at least a pair of control actuators. A timing mechanism including a counter is connected to the signal sources for selectively energizing one of the signal sources associated with a particular position of the counter in sequence with the other of the sources. Each pair of sensor selectors senses the physical property of the medium between its probes and develops a voltage proportionate to the value of the physical property of the medium between the probes.

10 Claims, 6 Drawing Figures

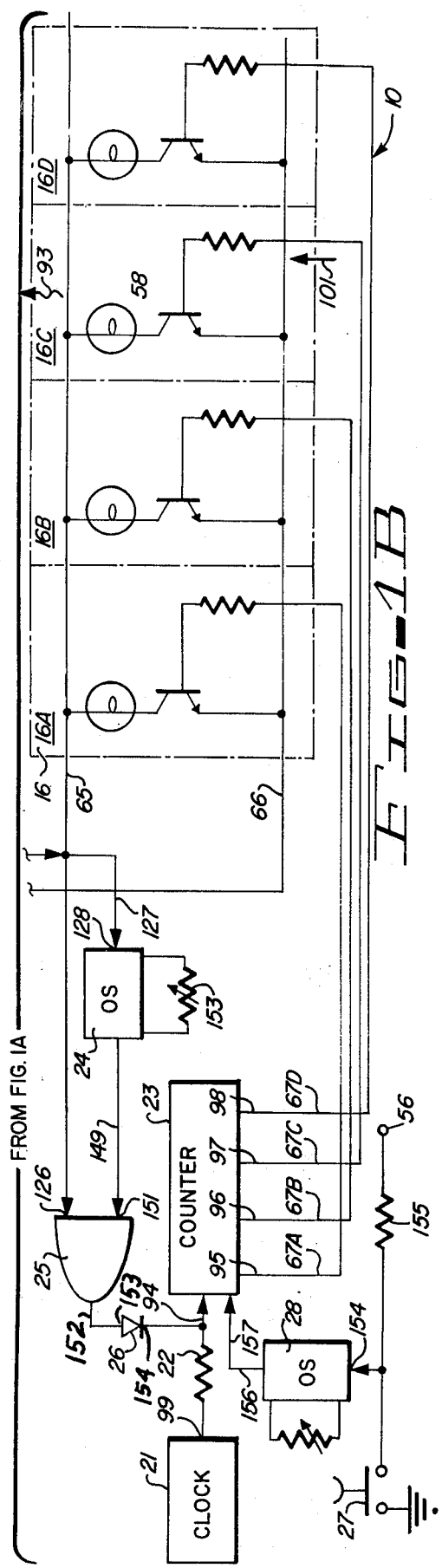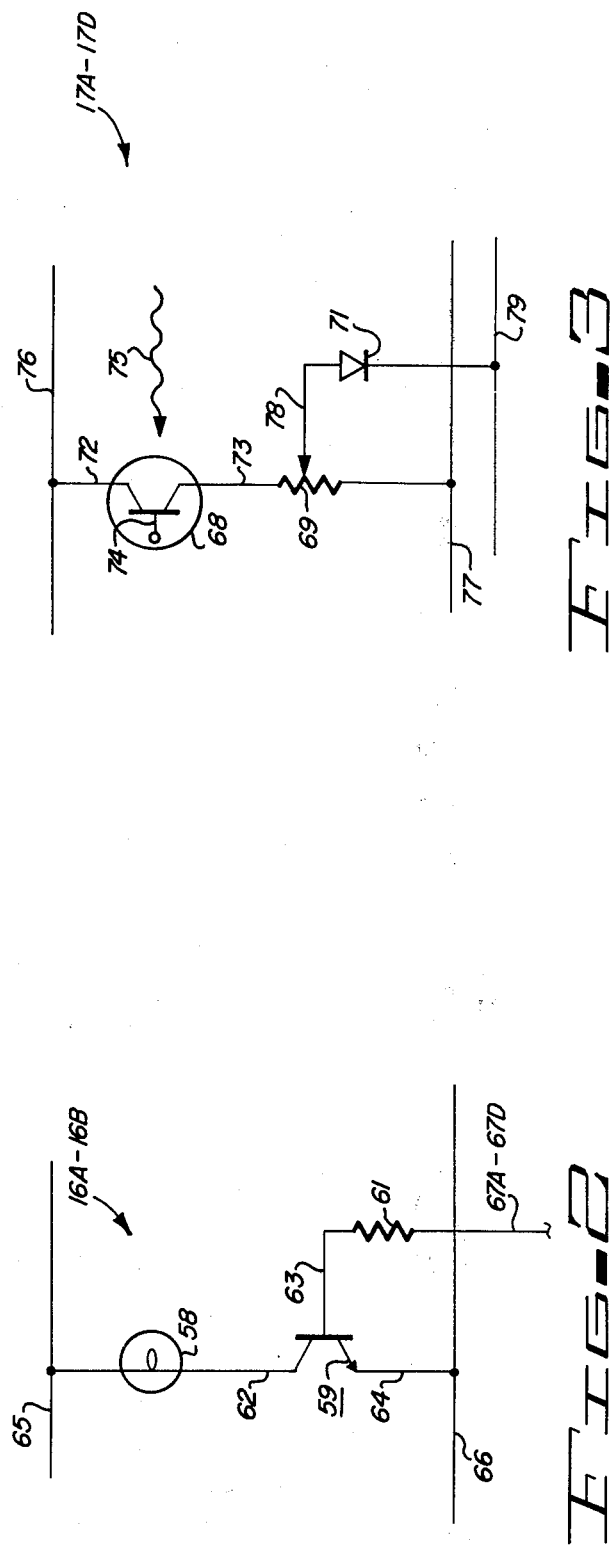

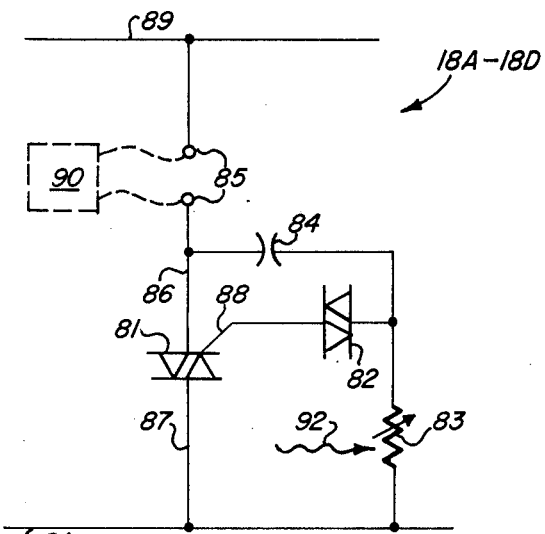
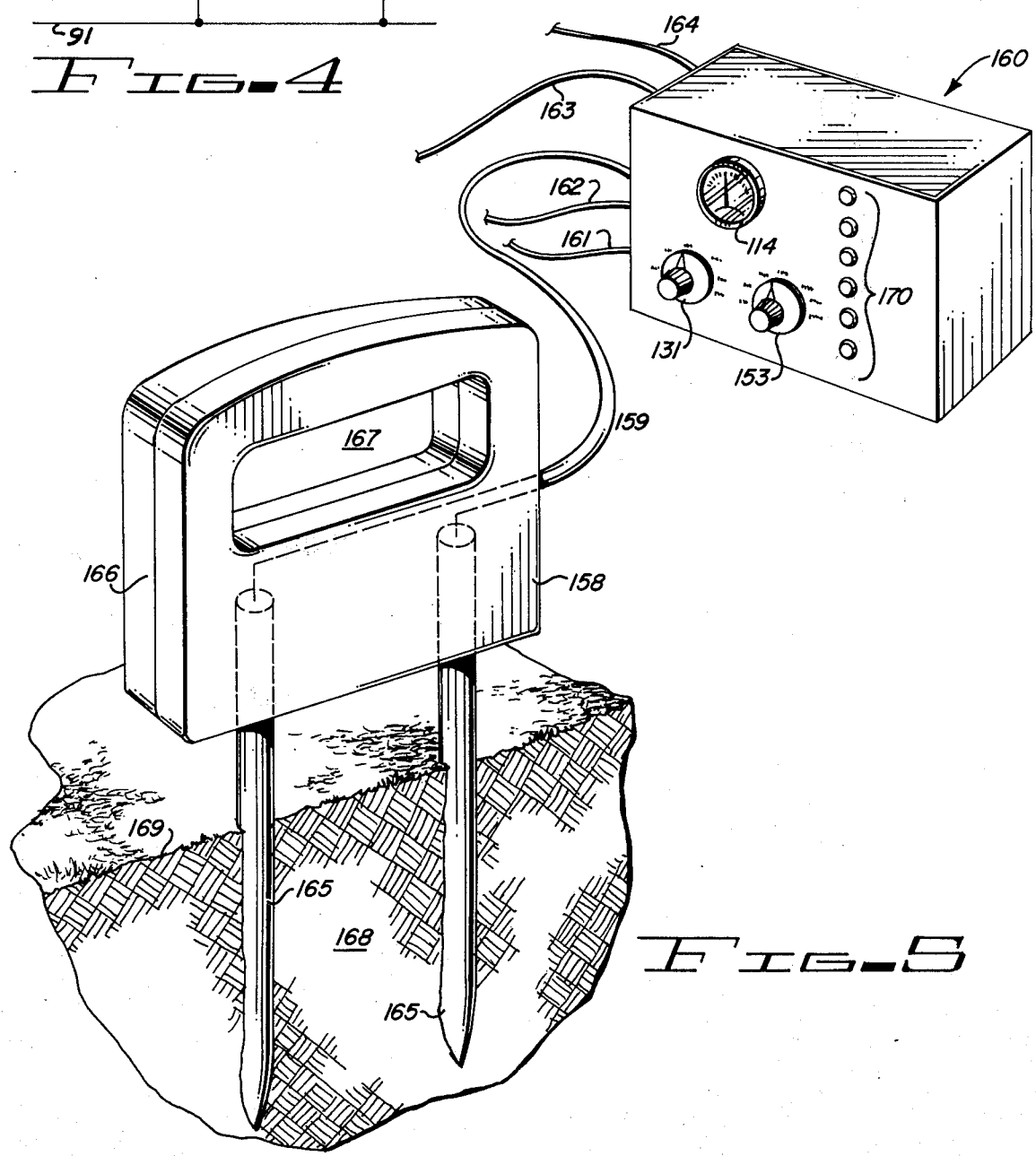

ANALOG SCANNER

BACKGROUND OF THE INVENTION

Although we tend to think of ourselves as living in an automated age, there are still many tasks and operations presently carried out manually which could be accomplished more efficiently and more effectively by an automatic control system. An example of particular interest in connection with this invention is the control of large-scale irrigation systems.

In the semi-arid and desert regions of the world, irrigation is required in one form or another to sustain vegetation, especially when plants are introduced that are not native to the particular location.

Once such vegetation has become established, it can very quickly wither and die if the irrigation is neglected even for a relatively brief period of time. Furthermore, improper irrigation methods which moisten the surface but do not penetrate the soil to a sufficient depth tend to foster improper root development which renders the plant even more susceptible to irrigation neglect. Such improperly watered plants are, in general, less vigorous than desired and are more vulnerable to disease.

The necessity of keeping a careful watch on irrigated fields, landscaping and gardens thus becomes a continuous obligation which ties down the farmer or homeowner, especially during the hot, dry summer months. In a typical large-scale irrigation system, he is obliged to water large areas a sector at a time, and constant attention is required for the opening and closing of valves associated with the individual sectors. An automatic means for ensuring proper watering in the absence of the operator will thus prove highly beneficial as a means for liberating him from this responsibility. In addition, if such automatic means can be made to optimize the irrigation operation, improved plant growth as well as economy in the use of available water can be realized. At a time when the food and water supplies of the country and the world are in such critically short supply, such an objective has become increasingly important.

There are numerous other industrial, domestic and agricultural operations of a similar nature which are amenable to the same type of automatic monitoring the control.

SUMMARY OF THE INVENTION

In accordance with the invention claimed, an automatic scanning system is provided which is capable of sequentially monitoring and controlling conditions at a number of remote points, thereby effectively and efficiently controlling certain types of industrial, agricultural or domestic operations.

It is, therefore, one object of this invention to provide an analog scanner with a capability for sequentially monitoring and controlling conditions at a number of remote points.

Another object of this invention is to provide such an analog scanner in a flexible and versatile form which is readily adaptable for the automatic control of a wide variety of industrial, agricultural and domestic operations for which such sequential control is appropriate.

A further object of this invention is to provide in such an analog scanner a specific capability for controlling an irrigation system in a scientific manner which results in optimum plant growth and reduced waste of the water supply.

A still further object of this invention is to provide such an analog scanner in a form which is compact in size, safe and easy to apply and inexpensive to own and operate.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWING

The present invention may be more readily described by reference to the accompanying drawing in which:

FIG. 2 is an enlarged schematic representation of one section of a bank of controlled light sources utilized to select associated sensors, actuators and control levels;

FIG. 3 is an enlarged schematic representation of one section of a bank of level controllers utilized in the scanner to set the desired control level associated with the condition of interest at one of the several remote points;

FIG. 4 is an enlarged schematic representation of one section of a bank of sensor selectors; and FIG. 5 is a pictorial representation of a particular application of the invention in which the analog scanner is employed to control an irrigation system.

DESCRIPTION OF THE PREFERRED EMBODIMENT

Figure 1A:
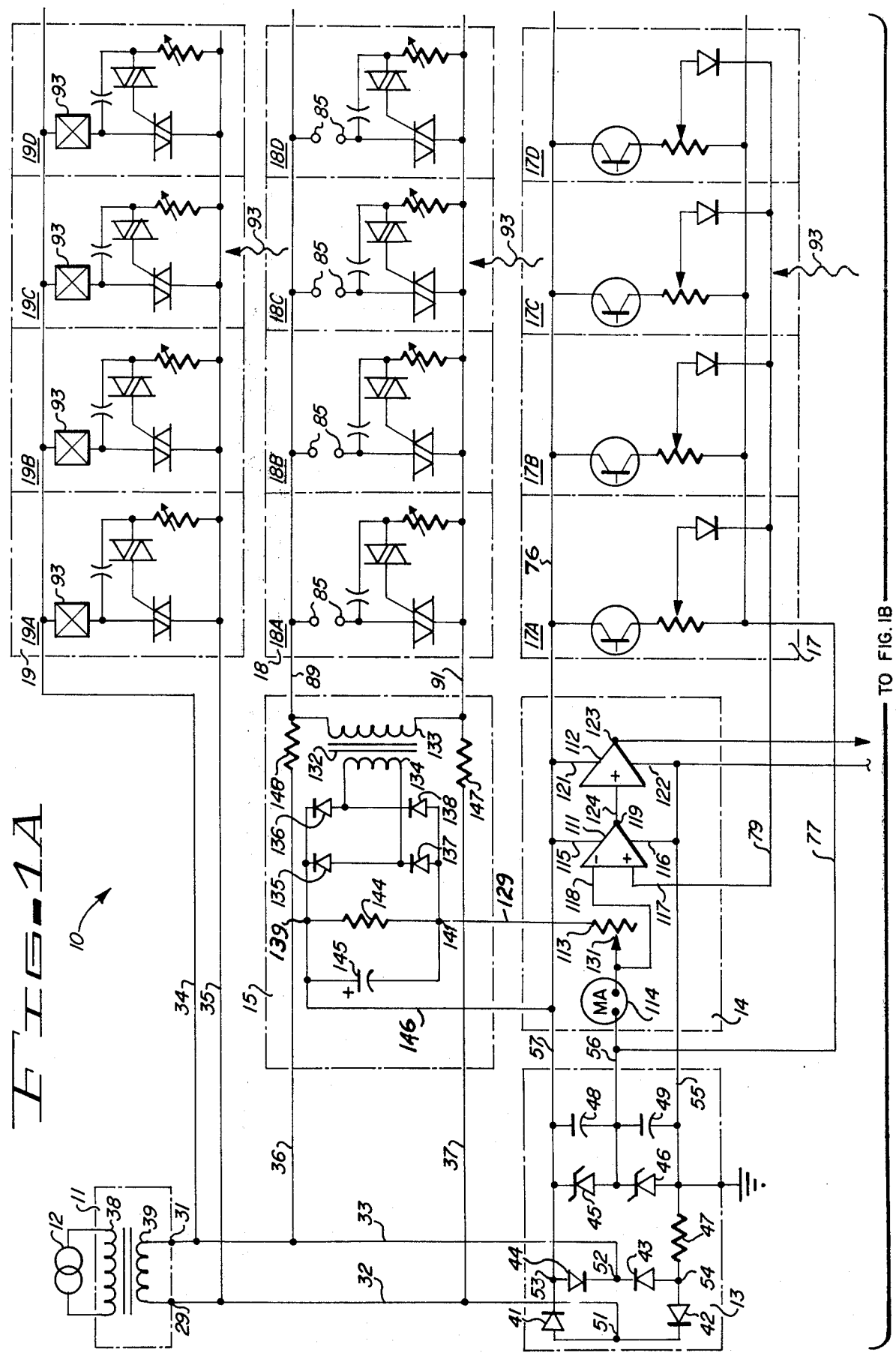
FIG. 1, comprising portions 1A-1B, discloses a schematic drawing of an analog scanner system.

Referring more particularly to the drawing by characters of reference, FIG. 1 illustrates an analog scanner system 10 embodying the invention, the system 10 comprising an isolation transformer 11 supplied by an alternating current source of voltage 12, a power supply 13, a comparator-regulator 14, an analog converter 15, a bank of controlled light sources 16, a bank of reference level controllers 17, a bank of sensor selectors 18, a bank of controlled actuators 19, a clock 21 and limiting resistor 22, a counter 23, an on-time limiting one-shot 24, an inhibitor gate 25 and auxiliary output diode 26, and a manual stepping switch 27 with its associated one-shot 28.

Isolation transformer 11 is a step-down transformer which converts the high input voltage from source 12 to a reduced and non-hazardous level of twenty-four volts or less at its output terminals 29 and 31. The reduced output voltage is carried by lines 32 and 33 to power supply 13; it is also carried by line 34 and 35 to the bank of controlled actuators 19 and by lines 36 and 37 to converter 15. Primary and secondary windings 38 and 39, respectively of transformer 11 are separated by electrical insulation so that the balance of the scanner system 10 is effectively isolated from the hazardous voltage supplied by source 12.

The power supply 13 comprises four rectifier diodes, 41 through 44, two zener diodes, 45 and 46, a resistor 47, and two filter capacitors 48 and 49.

Each of the rectifier diodes is represented by an arrow symbol, the point of the arrow representing the cathode and the tail of the arrow, the anode. The diodes pass current in the direction of the arrow and block current flow in the opposite direction. The four diodes are connected in a bridge configuration with the cathode of diode 42 connected to the anode of diode 41 to form a first a-c terminal 51 and the cathode of diode 43 connected to the cathode of diode 44 to form a second a-c terminal 52. The cathodes of diodes 41 and 44 are connected together forming the positive bridge terminal 53 and the anodes of diodes 42 and 43 are connected together forming the negative bridge terminal 54. The lines 32 and 33 from transformer 11 are connected, respectively, to a-c terminals 51 and 52.

The zener diodes are represented by modified arrows, the points again representing the cathodes and the tails the anodes. Zener diodes are characterized by their sharp reverse breakdown at a fixed voltage. This characteristic is utilized for the development of a regulated voltage by passing a reverse current through the zener diode from cathode to anode. In power supply 13 zener diodes 45 and 46 are serially connected, the cathode of diode 46 connected to the anode of diode 45. The cathode of diode 45 is connected to positive bridge terminal 53 and the anode of diode 46 is connected through series resistor 47 to negative bridge terminal 54. A d-c current flowing from positive bridge terminal 53 flows through diode 45, diode 46 and resistor 47 to develop roughly regulated d-c voltages across diodes 45 and 46. Capacitors 48 and 49 are connected across diodes 45 and 46, respectively, to filter the d-c voltages developed. The anode of diode 46 is brought out as ground terminal 55. The common point between diodes 45 and 46 is brought out as a first positive d-c output terminal 56, and the cathode of diode 45 is brought out as a second positive d-c output terminal 57.

Power supply 13 as just described is a conventional design of a type commonly employed to power electronic circuits.

The operation of the system 10 and much of the novelty of the analog scanner is involved in the interrelation of banks 16 through 19, each of which comprises a bank of circuits of a given configuration.

Bank 16 comprises a number of parallel-connected controlled light sources, four of which are shown in FIG. 1 where they are identified as sources 16A–16D. As shown in FIG. 2, each of the light sources 16A–16D comprises a lamp 58, an NPN transistor 59 and a resistor 61.

A variety of lamp types may be employed as lamp 58 including incandescent, light emitting diodes, neon, etc.

Transistor 59 is a conventional NPN device having a collector 62, a base 63 and an emitter 64. A high collector-emitter resistance is present when base 63 is held at a low or slightly negative potential with respect to emitter 64 so that no current flows into base 63. When the potential of base 63 is raised to a positive value with respect to emitter 64 so that a positive base-emitter current is achieved, the collector-emitter resistance falls to a low value for a range of collector-emitter currents.

As shown in FIG. 2, the lamp 58 is connected between the collector 62 of transistor 59 and a positive voltage line 65. The emitter 64 of transistor 59 is connected to line 66 which is connected to ground terminal 55 of power supply 13. Base 63 is connected through resistor 61 to a line 67A–67D which is unique for each of the light sources 16A–16D. When a positive voltage is present on line 65 and line 67A–67D is raised to a sufficiently positive voltage with respect to ground line 65, transistor 59 turns on and lamp 58 is energized. It should be recognized that more than one lamp may be connected in place of the single lamp 58 so that individual lamps appropriately located may be utilized if desired to enable level controllers, sensor selectors and actuators.

Bank 17 comprises a number of parallel-connected reference level controllers, four of which are shown in FIG. 1 as controllers 17A–17D. As shown in FIG. 3, each of the controllers 17A–17D comprises a photo-transistor 68, a potentiometer 69 and a diode 71.

The photo-transistor 68 has a collector 72, an emitter 73 and a base 74. The base 74 may be left unconnected as shown or it may be connected to a biasing circuit. Transistor 68 is constructed with a transparent housing so that incident light rays 75 may strike the emitter-base junction. With no light striking the emitter-base junction, the transistor 68 has a high collector-emitter resistance; when incident light is present, the collector-emitter resistance is low. Such devices are readily available from semiconductor manufacturers and a more detailed technical description is given in the General Electric Co. SCR Manual, Fifth Edition, 1972, p. 411.

As shown in FIG. 3, the collector 73 is connected to a positive voltage line 76 and emitter 73 is connected to one end of potentiometer 69. The other end of potentiometer 69 is connected to a line 77 which is connected to positive d-c output terminal 56 of supply 13 as shown in FIG. 1. The anode of diode 71 is connected to the brush 78 of potentiometer 69 and the cathode of diode 71 is connected to a line 79. Lines 76, 77 and 79 are common to all four level controllers, 17A–17D.

If the transistor 68 in any one of the controllers 17A–17D is struck by light rays 75, the transistor is turned on, a current flows from line 76 through transistor 68 and potentiometer 69 to line 77, and a voltage is developed across potentiometer 69. A portion of the voltage developed is picked up by brush 78 and is coupled through diode 71 to line 79. The diodes 71 in the other of the converters 17–17D not struck by light rays 75 block voltage coupled to line 79 and these other controllers are thereby prevented from shunting or absorbing the voltage on line 79.

Bank 18 comprises a number of parallel-connected sensor selectors, four of which are shown in FIG. 1 as selectors 18A–18D. As shown in FIG. 4, each of the selectors 18A–18D comprises a triac 81, a diac 82, a photo-sensitive resistor 83, a capacitor 84 and a pair of terminals 85.

Triac 81 has a first main terminal 86, a second main terminal 87 and a gate 88. Triac 81 offers a high a-c impedance between first and second main terminals 86 and 87 unless a positive or a negative trigger pulse if applied to gate 88. Upon the introduction of such a gate pulse the triac 81 switches to a low impedance and it remains in the low impedance state until the current goes to zero. In a typical application the gate pulse is applied at some point in each half cycle of applied a-c voltage to sustain an a-c current through the triac. A more detailed explanation of the construction and operation of the device is given in the General Electric SCR Manual referenced earlier, beginning on page 182 of the manual.

The diac 81 is a semiconductor device commonly employed to trigger triacs. A description of the device and its applications is given in the General Electric Co. SCR Manual, Fifth Edition, pp. 25, 110, 183, 192. Very briefly, the diac is a bilateral semiconductor device which switches from a high impedance to a low impedance as its break-over voltage, typically about 20 volts is exceeded.

Photo-sensitive resistor 83 is a resistance device having a value of resistance which is very substantially reduced by light rays 92 striking its surface. Photoconductive devices of this type have long been known to the art. A detailed description of this phenomenon as exhibited by selenium devices is given on pp. 174–176 of *Industrial Electronics and Control*, Kloeffler, Copyright 1949, John Wiley and Sons, Inc.

As shown in FIG. 4, the triac 81 and the pair of terminals 85 are serially connected between lines 89 and 91, the second main terminal 87 of triac 81 being connected to line 91. Terminal pair 85 is connected between first main terminal 86 and line 89. Photo-sensitive resistor 83 has one end connected to line 91 and its other end connected to a first terminal of capacitor 84 and to a first terminal of diac 82. The second terminal of capacitor 84 is connected to first main terminal 86 of triac 81 and the second terminal of diac 82 is connected to gate 88 of triac 81. A load 90, in this case a sensor element, is connected across terminal pair 85. The circuit configuration just described is commonly employed as a trigger circuit for triacs and is illustrated on page 192 of the General Electric SCR Handbook referenced earlier. The only difference between the configuration of FIG. 4 and the illustrated circuit on page 192 of the Handbook is that in FIG. 4 a photo-sensitive resistor is employed in place of the manually-adjustable resistor shown in the Handbook.

In operation, the capacitor 84 is charged each half cycle of applied a-c voltage until its charge equals the break-over voltage of diac 82, whereupon diac 82 switches to a low impedance, passes current to gate 88 of triac 81, thereby turning on triac 81 for the remainder of the half cycle. If resistor 83 has a high resistance value as when no light rays are present, the capacitor will not reach the break-over voltage of the diac and the diac as well as the triac will not be turned on. When light rays 92 strike resistor 83 the value of resistance is low enough to produce turn-on of the diac and the triac.

Bank 19 comprises a number of parallel-connected controlled actuators, four of which are shown in FIG. 1 as actuators 19A–19D. The controlled actuators 19A–19D are the same as selectors 18A–18D except that an actuator solenoid 93 is connected as the load 90 of FIG. 4.

As indicated in FIG. 1, for each light source, 16A–16D there is a corresponding level controller 17A–17D, a corresponding sensor selector 18A–18D, and a corresponding controlled actuator 19A–19D. If one of the light sources is energized as, for example, source 16C, light rays 93 as shown in FIG. 1 strike the photo-transistor of level controller 17C and the photo-sensitive resistors of selector 18C and actuator 19C enabling these three circuits simultaneously.

The function of the clock 21 and the counter 23 is to energize each of the light sources 16A–16D, one at a time in a sequential manner, A, B, C, D, A, B, C, D, etc.

Counter 23 is available as an integrated circuit of a type commonly referred to as a ripple counter. Typically it has an input trigger terminal 94 and a number of output terminals, four being shown in FIG. 1 as terminals 95, 96, 97 and 98. At any given instant of time one of the output terminals 94 through 98 has a positive value and all the other output terminals are at or near zero or ground potential. When the next trigger pulse occurs at terminal 94, the one output terminal that had been at a positive level is switched to zero and the next-in-order output terminal switches to a positive level. In the case of the counter here employed a negative-going trigger pulse is required.

The clock 21 may be assembled from discrete components or a commercially available integrated circuit may be employed. In the discrete version, a unijunction relaxation oscillator driving an NPN transistor may be employed, taking the output signal from the collector of the transistor. In this way an output signal may be produced which is positive except for a brief period at the end of each timing cycle when it falls to a value near zero volts.

The output terminal 99 of the clock is connected to the trigger input terminal 94 of the counter 23 through the limiting resistor 22 and each of the output terminals 95 through 98 is connected respectively to one of the lines 67A–67D which, in turn, are connected, respectively, to the light sources 16A–16D. Thus, for example, when output 97 switches to a positive level a current 101 flows over line 67C to turn on the transistor 59 of source 16C to energize its lamp 58 and thereby enable circuits 17C, 18C and 19C as described earlier.

Operating in conjunction with the selected members of the banks 16 through 19 in the control of counter 23 as appropriate for regulating a particular industrial, agricultural or domestic system are the converter 15, the comparator regulator 14, the one-shot 24 and the gate 25. Descriptions of these individual elements now follow:

The comparator-regulator 14 comprises a differential amplifier 111, a non-inverting buffer amplifier 112, a potentiometer or variable resistor 113 and a d-c miliammeter 114. Amplifiers 111 and 112 are built around conventional integrated circuits. For differential amplifier 111 an LM 307 is appropriate; buffer amplifier 112 may utilize a type 54 power driver. These two commercially available integrated circuits are available from Signetics Corporation and are described in their Integrated Circuits Handbook (Digital/-Linear/MDS), copyright 1972, pages 6-175 through 6-178 (Lm307) and pages 6-36 through 6-44 (540). Additional resistive and capacitive components required in conjunction with the 540 amplifier are suggested in the Handbook.

Differential amplifier 111 has a positive power connection 115, a negative power connection 116, a non-inverting input terminal 117, an inverting input terminal 118, and an output terminal 119. The amplifier is designed to produce at its output terminal the highly amplified differences between the signals applied at the two input terminals. Thus, if the signal at the non-inverting input terminal 117 is more positive than the signal at the inverting input terminal 118, a high positive signal will be delivered at output terminal 119; if terminal 118 is positive with respect to terminal 117 the output terminal will be at a low voltage level near the potential of the negative power connection 116.

The buffer amplifier 112 also has positive and negative power connections 121 and 122, respectively, an output terminal 123 and a non-inverting input terminal 124. This amplifier is designed so that the voltage at the output terminal 123 follows the voltage at input terminal 124, the amplifier providing power amplification only with a high current capability provided at its output.

As shown in FIG. 1 the positive power connections 115 and 121 of amplifiers 111 and 112 are tied to terminal 57 of power supply 13 and negative power connections 116 and 122 are tied to ground terminal 55. Voltage line 76 of reference level controllers 17A–17D is also tied to terminal 57 and line 79 which carries the selected reference level is connected to non-inverting terminal 117 of amplifier 111. Output terminal 119 of amplifier 111 is connected to input terminal 124 of buffer amplifier 112 and output terminal 123 of amplifier 112 is connected to line 65 which is the common positive voltage line of light sources 16A–16D and which is also tied by line 125 to a first input terminal 126 of gate 25 and by line 127 to the input terminal 128 of one-shot 24. Potentiometer 113 has one end connected to a line 129 which delivers an output signal from converter 15, its opposite end is free, and its brush 131 is connected to inverting terminal 118 of amplifier 111 and also to one terminal of milliammeter 114. The other terminal of milliammeter 114 is connected to terminal 56 of power supply 13 along with line 77 from level controllers 17A–17D.

Converter 15 comprises a transformer 132 having a primary winding 133 and a secondary winding 134, four diodes 135–138 connected in a bridge configuration with positive and negative bridge terminals 139 and 141, respectively, and with a-c bridge terminals 142 and 143, a secondary load resistor 144 connected across terminals 139 and 141, and a filter capacitor 145 connected in parallel with resistor 144. Capacitor 145 has its positive plate connected to positive bridge terminal 139 and to a line 146 which is tied to terminal 57 of power supply 13. Primary winding 133 is connected to lines 89 and 91 of sensor selectors 18A–18D. Winding 133 is also connected to winding 39 of transformer 11 through series limiting resistors 147 and 148 and through lines 36 and 37, 33 and 32.

One-shots 24 and 28 are timing circuits of a type which responds to an input trigger signal by delivering an output pulse of a fixed duration. The duration of the output pulse is determined by a resistance-capacitance network. An integrated circuit commonly employed as a one-shot is the 555 timer which is available from a number of manufacturers. Its specifications and characteristics are given on pages 6-49 to 6-55 of the Signetics Handbook referenced earlier. The output of the 555 timer is low in the static condition and it rises to a positive level when a negative trigger pulse is applied to its input terminal. The period of time during which the output remains at the positive level is controllable by means of a resistance-capacitance network which is connected external to the 555 integrated circuit.

The input terminal 127 of one-shot 24 is connected as mentioned earlier to the output terminal of buffer amplifier 112 and the output terminal 149 of one-shot 24 is connected to the second input terminal 151 of gate 25.

Gate 25 is an AND gate which is commonly employed in computer logic circuits. It has two input terminals 126 and 151 as referenced earlier and an output terminal 152. The output terminal is at a low voltage level unless both input terminals are at a high positive level. Integrated circuit type 7408 has four two-input AND gates in a single package. Specifications for the 7408 integrated circuit are given on pages 2-18 and 2-19 of the Signetics Handbook referenced earlier.

The output terminal 152 of gate 25 is connected to the anode 153 of diode 26, and the cathode 154 of diode 26 is connected to input terminal 94 of counter 23 so that when the output of gate 25 is "high", i.e. at a positive level the input terminal 94 of counter 23 is held positive by gate 25 and clock 21 is prevented from setting the next condition of counter 23.

OPERATION

The overall operation of the analog scanner system 10 will now be described with reference to a particular assumed application, i.e. as a controller for an irrigation system. For this application, it will be assumed that the sensors connected at terminals 85 of sensor selectors 18A–18D are resistance probes which are driven into the soil at various points in the fields which are to be irrigated, the resistance between the probes being inversely proportional to the moisture content of the soil. Also in this application, it will be assumed that the controlled actuators 19A–19D open irrigation valves when they are energized and that actuators and sensors of similar alphabetical identification are associated together, e.g. the sensor connected to selector 18A monitors moisture in the area that is irrigated by actuator 19A, etc.

When power is first applied one of the output terminals 95–98 of counter 23 will be positive. Assuming that terminal 97 is positive, a current flows from this terminal through line 67C to enable light source 16C. Light rays 93 from lamp 58 of source 16C enable level controller 17C, sensor selector 18C and actuator 19C. Because triac 81 of sensor selector 18C has been turned on by light from source 16C, a current now flows from line 36 through resistor 148, through the sensor connected across terminals 85 of selector 18C, through the turned-on triac 81 of selector 18C and through resistor 147 and line 37 to line 32. If the soil is dry in the area where the sensor is installed its resistance will be high and a relatively large voltage will be developed across terminals 85. This relatively large voltage appears also across primary winding 133 and by transformer action across secondary winding 134 of transformer 132. The transformed voltage across winding 134 is rectified by diodes 135–138 and filtered by capacitor 145, the filtered d-c voltage thus appearing across capacitor 145 being representative of and inversely proportional to the moisture content of the soil as monitored by the sensor.

The positive plate of capacitor 145 is connected to power supply terminal 57 and the negative plate of capacitor 145 is tied to the upper end of potentiometer 113 so that the voltage across capacitor 145 is subtractive from the power supply voltage driving current through potentiometer 113 and meter 114. Thus, as soil moisture content increases and capacitor 145 voltage correspondingly decreases, the current through potentiometer 113 and milliammeter 114 increase. It is seen then that increasing moisture content produces increased milliammeter current and also an increase in voltage at potentiometer brush 131 and hence also at input terminal 118 of amplifier 111.

At low moisture levels the voltage at terminal 118 will be below the reference voltage present at input terminal 117 and in accordance with the operation of amplifier 111 as discussed earlier, the signals at output terminals 119 and 123 of amplifiers 111 and 112 will be high. As water continues to flow to the irrigated area monitored by the selected sensor, the voltage at terminal 118 becomes increasingly positive until it finally becomes more positive than the voltage at terminal 117. At this point, the voltages at output terminals 119 and 123 fall to a low value near zero, light source 16C is extinguished, the voltage at terminal 126 of gate 25 falls to a level near zero, output terminal 152 of gate 25 falls to a low value and the next pulse occurring at the output of clock 21 sets counter 23 to its next state which raises output terminal 98 to a positive level as terminal 97 falls to zero. A current now flows from terminal 98 through line 67D to enable light source 16D and consequently also level controller 17D, sensor selector 18D and actuator 19D.

The point at which the voltage at terminal 118 exceeds the voltage at terminal 117 of amplifier 111 is controllable by the adjustment of potentiometer 69 of the selected level controller 16A, 16B, 16C or 16D. If a relatively high moisture level is desired, the brush 78 is moved upward toward the end of potentiometer 69 that is connected to transistor 68. Individual adjustments are thus possible for each of the monitored irrigation sectors. Potentiometer 113 also provides a common adjustment which is useful in calibrating the miliammeter 114 so that its reading properly indicates moisture content at any given time. Potentiometer 113 should be adjusted prior to the adjustment of the several potentiometers 69.

Because of the possibility of faulty operation, it is always possible that the system might "hang up" at a given position so that an irrigation valve remains energized long after the desired moisture level is achieved. To prevent such a condition from persisting indefinitely with catastrophic results, one-shot 24 has been included to terminate any given enabled state after a fixed period of time. Thus, for example, resistor 153 which controls the period of one-shot 24 may be adjusted to give a one-shot period of fifteen minutes. If the output signal of amplifiers 111 and 112 fail to fall at the end of fifteen minutes, the output of one-shot 24 will fall causing terminal 151 of gate 25 to fall. Output terminal 152 then falls to a low voltage also, allowing the next pulse from clock 21 to set the next state of counter 23.

In the serving and adjustment of the scanner system 10 the operator or technician may wish to pulse the counter 23 manually to select successive operating states. To permit such manual intervention the pushbutton switch 27 and the one-shot 28 are provided.

When switch 27 is open input terminal 154 of one-shot 28 is held at a positive level by virtue of its connection to power supply terminal 56 through a resistor 155. When switch 27 is closed momentarily terminal 154 is shorted to ground and one-shot 28 is thus triggered, its output becomes positive for its time-out period and then as it falls again to zero the counter 23 is set to the next condition. The period of one-shot 28 is set only long enough to persist through any possible contact-bouncing interval associated with the closing of switch 27 so that counter 28 will be advanced only one step rather than several as might otherwise result from the bouncing contacts had switch 27 been connected directly to counter 23. The output terminal 156 of one-shot 28 is connected to a separate input terminal 157 of counter 23.

FIG. 5 gives a physical representation of the scanner system 10 as applied to an irrigation system. An enlarged moisture sensor 158 is shown connected by a pair of lines 159 to analog scanner assembly 160. Additional sensors are connected to lines 161–164. Scanner assembly 160 contains the system 10 of FIG. 1. Shown on the face of assembly 160 are the milliammeter 114, potentiometer 113, one-shot adjusting resistor 153, and level adjustment potentiometer 69. Additional front-panel adjustments may be provided including the period of clock 21 which is adjustable also by means of a potentiometer.

The sensor 158 is a simple assembly including two sharpened electrically conductive prongs 165 which are held in parallel relationship with each other by means of an insulative rectangular clamp 166 which has an oblong cutout 167 arranged to serve as a handle. The lines 159 are connected internally to the tops of the prongs 165 and are brought out the side of the clamp 166. To monitor soil moisture the prongs 165 are thrust into the soil 168 to a desired depth below the surface 169.

While the analog scanner system as just described is thus shown to be ideally suited for application in an irrigation system, it is to be emphasized that the system is not intended to be limited to this application. It is equally well suited to other applications including heating and cooling with multiple control locations, chemical processing plants, etc. Only minor differences from application to application will be required. These will involve the sensors and the actuators and little else.

Although but a single embodiment of the invention has been illustrated and described, it will be apparent to those skilled in the art that various changes and modifications may be made without departing from the spirit of the invention or from the scope of the appended claims.

What is claimed is:

1. An analog scanner for at least two pairs of probes utilized for measuring a physical property of a medium therebetween comprising:
    a power supply,
    at least a pair of control signal sources,
    at least a pair of reference level controllers,
    at least a pair of sensor selectors,
    at least a pair of control actuators,
    means for connecting said signal sources, reference level controllers, sensor selectors and control actuators to said power supply for energization thereof,
    a timing mechanism,
    a counter connected to said timing mechanism for movement through a counting cycle,
    means for connecting said counter to said pair of signal sources for selectively energizing one of the signal sources associated with a particular position of said counter in sequence with the other of said sources,
    the signals from said one of said signal sources enabling an associate one of the pairs of level controllers, sensor selectors, and controller actuators,
    each of said sensor selectors comprising a pair of probes,
    said enabled sensor selector senses the physical property of the medium between said probes and develops a voltage across said pair of probes proportionate to a value of the physical property of the medium between said probes,
    said associated level controller sensing at least a portion of the voltage appearing across said pair of probes and transmitting signals to a voltage comparator when energized by a particular voltage appearing across said probes,
    said associated controller actuator upon enabling thereof providing a signal for implementing a given control function, and
    a voltage comparator regulator means energized by said power source and connected to receive signals from said probes and said associated level controller for comparing analog values of signals from the probes with signals from said associated level controller and generating signals responsive to conditions of the medium sensed, said generated signals determining the energization of said one of said signal sources.

2. The analog scanner set forth in claim 1 wherein:
said signal sources comprises a pair of light sources whereby the light rays from said one of said light sources enables an associated one of the pairs of level controllers, sensor selectors, and control actuators.

3. The analog scanner set forth in claim 1 in further combination with:
an isolation transformer supplied by an alternating current source of voltage, and wherein said power supply is energized by a reduced output voltage of said transformer.

4. The analog scanner set forth in claim 1 wherein:
said timing mechanism comprises a multi-vibrator.

5. The analog scanner set forth in claim 2 wherein:
said light sources, level controllers, sensor selectors and control actuators each comprise a plurality of like devices one of each plurality associated with one of each of the other devices.

6. The analog scanner set forth in claim 1 in further combination with:
a second timing circuit connected to said signal source and said counter for energizing said counter after a predetermined time causing it to move to the next stage of the counter.

7. The analog scanner set forth in claim 6 wherein:
said second timing circuit comprises a one-shot device which has a fixed action time.

8. The analog scanner set forth in claim 1 wherein:
each of said level controllers being provided with individual adjustments for controlling its energization by the voltage appearing across said probes.

9. The analog scanner set forth in claim 1 wherein said scanner is utilized to measure the resistance of soil conditions existing between pairs of probes extending thereinto wherein:
said enabled sensor selectors senses the resistance of the ground existing between said probes and develops a voltage across said pair of probes inversely proportionate to the moisture content of the ground between said probes.

10. The analog scanner set forth in claim 1 in further combination with:
a pulsing means connected to said counter for actuating said counter independently of said timing mechanism to any counter setting.

* * * * *